United States Patent [19]

Glück et al.

[11] Patent Number: 5,006,335

[45] Date of Patent: Apr. 9, 1991

[54] LIVE VACCINE AGAINST MUMPS AND PROCESS FOR OBTAINING THEREOF

[75] Inventors: Reinhard Glück, Köniz; René Germanier, Bern, both of, Switzerland

[73] Assignees: Swiss Serum & Vaccine Institute; Institute for the Research of Infectious Diseases, both of Berne, Switzerland

[21] Appl. No.: 905,925

[22] Filed: Sep. 10, 1986

[30] Foreign Application Priority Data

Nov. 26, 1985 [CH] Switzerland .................. 05062/85
Jan. 15, 1986 [CH] Switzerland .................. 00133/86

[51] Int. Cl.$^5$ .................. A61K 39/12; C12N 7/00
[52] U.S. Cl. .................. 424/89; 424/86; 424/93; 435/235.1; 435/236; 435/237
[58] Field of Search .................. 424/89, 86, 93; 435/235, 236, 237

[56] References Cited

U.S. PATENT DOCUMENTS

| | | | |
|---|---|---|---|
| 3,514,374 | 5/1970 | McAleer et al. | 424/89 |
| 3,555,149 | 1/1971 | Buynak et al. | 424/89 |
| 3,829,361 | 8/1974 | Hoshino et al. | 424/89 |
| 3,961,046 | 6/1976 | Cerini | 424/89 |
| 4,324,861 | 4/1982 | Kan | 424/89 |

OTHER PUBLICATIONS

CMAJ 138: 135 (1988).
Lancet, p. 394 (Aug. 12, 1989).
Esact Meeting 8th: 1987, p. 587.
Canada Diseases, Weekly Report, p. 209 (1988).
Canada Diseases, Weekly Report, p. 155 (1987).
Lancet, p. 677, Sep. 16, 1989.
Lancet, p. 751, Sep. 23, 1989.
BMJ, 299: 660 (1989).

*Primary Examiner*—Margaret Moskowitz
*Assistant Examiner*—Abdel A. Mohamed
*Attorney, Agent, or Firm*—Bradford E. Kile

[57] ABSTRACT

The invention relates to a live vaccine against mumps, which contains live mumps viruses which are capable of multiplication and have been attenuated principally by passages in diploid human tissue cultures. The vaccine is substantially free from proteins and antibiotics.

The invention also relates to the process for the preparation of a live vaccine against mumps, which comprises obtaining live mumps viruses from the urine of patients with an acute attack of mumps, passaging the viruses in diploid human cells, thereby attenuating the viruses by repeated passages in tissue of this type and, optionally further attenuating the viruses by passaging in embryonic or fertilized chicken eggs, optionally further attenuating the viruses by further passaging in diploid human cells, thereby adapting the viruses to human tissue, isolating, cultivating, and then processing the live mumps viruses.

6 Claims, No Drawings

LIVE VACCINE AGAINST MUMPS AND PROCESS FOR OBTAINING THEREOF

BACKGROUND OF THE INVENTION

1. Field of the Invention

The invention relates to a live vaccine against mumps which is adapted to human cells, and to a process for the preparation thereof from virulent mumps viruses obtained from patients suffering from an acute attack of mumps.

2. Description of the Background

Mumps or epidemic parotitis is a very widely disseminated infectious disease which in many cases, hardly causes any symptoms other than swelling of the parotid glands. The disease usually has a benign course in childhood.

After puberty the incidence of complications is sharply increased. For example, orchitis (in men) and ovaritis (in women) which may result in atrophy of the respective organs, sometimes to the extent of causing sterility, are observed. Other complications of this viral infection may affect the central nervous system and cause encephalitis, encephalomyelitis, neuritis and meningitis.

The highest incidence of the disease occurs with school age children. The infection rate is highest at this age. An incubation period of 18 to 21 days is followed by the acute febrile phase. The infectivity starts 2 days before the swelling of the glands and lasts until the swelling subsides. In the aftermath, life-long immunity is conferred on those who have recovered from the disease.

In view of the possible complications brought about by mumps attacks, especially in adults, the availability of an optimally tolerated live mumps vaccine capable of eliciting a high antibody titer is highly desirable. Where possible, vaccination is to be carried out in the first to the third year of life.

A process for culturing viruses which provide a mumps live vaccine is described in Swiss Patent Specification 475,355. This process comprises subjecting virulent mumps viruses to several passages in chicken embryo tissue culture until it is appropriately attenuated.

In principle, this process has the disadvantage that in a live vaccine prepared in this manner, the viruses have been adapted to chicken embryo tissue culture cells and still contain residues of materials from these cells. It is known that foreign proteins in the inoculated liquid may cause undesired hypersensitivity reactions in a patient. Moreover, the vaccine produced in chicken embryo tissue cultures contain undesired antibiotics such as, e.g., neomycin, which are required to prevent bacterial contamination.

Therefore, a need continues to exist for a mumps vaccine and a method of preparing a mumps vaccine containing live attenuated mumps viruses which is free from non-human proteins and antibiotics to avoid the side effects of the known vaccines.

SUMMARY OF THE INVENTION

The invention provides a live vaccine against mumps, which comprises live mumps viruses capable of being multiplied which are attenuated by passaging, principally in diploid human tissue cultures.

In another feature, the invention provides a vaccine containing attenuated mumps viruses of the Rubini strain, deposited at the Institute Pasteur, Collection Nationale de Cultures de Microorganismes (C.N.C.M.), 25 rue du Docteur Roux, 75724 Paris Cedex 15, France, on Jan. 14, 1986, file number I-503).

In another aspect, the present invention also provides a process for the preparation of the live vaccine against mumps, comprising obtaining viruses from body fluids of a subject undergoing an acute attack of mumps, said viruses capable of being multiplied; and attenuating the viruses by multiple passages in diploid human tissue.

In a further aspect of the invention, the process further comprises further attenuating the diploid human cell-attenuated viruses by multiple passages in embryonic poultry eggs, e.g., chicken eggs.

In still another aspect, the process further comprises further attenuating the embryonic poultry egg-attenuated viruses by multiple passages of the viruses in diploid human cells. The thus obtained viral preparation may then be cultivated (multiplied) and, finally, further purified and processed to give the live vaccine by methods known in the art.

In still another aspect of the invention, the already attenuated viruses by multiple passages in human diploid cells and in embryonic poultry eggs, may be further attenuated by multiple passages in human diploid cells.

DESCRIPTION OF THE PREFERRED EMBODIMENTS

The invention provides a mumps vaccine comprising live mumps viruses having been obtained from body fluids of a subject affected by an acute attack of mumps; said viruses having been attenuated by passaging in at least diploid human culture cells. The mumps vaccine of the invention does not have the disadvantages of the prior art vaccines, elicits high antibody titers, is optimally tolerated, stimulates no local or systemic hypersensitivity reactions and contains no pharmacologically active constituents other than from attenuated harmless mumps viruses.

This invention originated from the finding that mumps viruses obtained from patients suffering from an acute attack of mumps can be cultured on diploid human tissue, can be attenuated and adapted by repeated passages in this tissue and by passages in the amniotic and allantoic sac of embryonic or fertilized poultry eggs, e.g., chicken eggs, optionally followed by further passaging in diploid human tissue culture, and thus provide a live vaccine against mumps.

To obtain an effective vaccine it is convenient, in passaging the viruses through various tissue cultures, to select for further processing, at each step, viruses from passages evidencing a particularly high titer.

In one embodiment of this invention, the Rubini mumps virus strain, which was obtained from the urine of an eight-year old boy suffering from an acute attack of mumps, was attenuated and adapted using this method by passaging in diploid human cell cultures. A seed strain of the Rubini type suitable for production of vaccine was selected from the thus obtained material.

The selected mumps virus strain thus obtained is distinguished by a very high multiplication rate in human tissue, rapid development of especially high antibody titers in humans, and its being well tolerated and problem-free when administered to humans.

The thus obtained human diploid cell (HDC) live vaccine against mumps contains substantially no foreign animal proteins and no antibiotics.

DETAILED DESCRIPTION OF THE PREPARATION OF MUMPS VACCINE

A—Isolation and transfer of virulent mumps virus

The isolation of the virus from urine from a patient suffering from mumps is carried out by ultracentrifugation for 4 hours at 25,000×r.p.m. The fraction containing mumps virus which is thus obtained (as determined by a hemagglutination test), is cultured in tissue culture of diploid human cells (e.g., cultures of the Wi-38 type) and in poultry eggs, e.g., chicken eggs which have undergone initial incubation. (Wi-38 cells are deposited with Flow Lab. under the number CCL 75). The thus isolated mumps virus is then purified and concentrated by ultracentrifugation (for 4 hours at 25,000×r.p.m.).

B—Attentuation and adaptation

For further attenuation and adaptation to growing in human tissue, the above mumps seed virus was subjected to further passages in fertilized chicken egg and again in human diploid cells, as follows, by (1) several passages in the amniotic or allantoic sac of embryonic poultry eggs, or alternatively, a temperature between about 30° and 35° C. (for example 32° C.) of chicken eggs which had undergone initial incubation, (2) further passages in diploid human cell tissue such as the MRC-5 type at about 30° C., and (3) new passages in tissue cultures of cells of the same type (MRC-5) at 35° C.

C—Preparation of the vaccine

The seed virus obtained after these successive passages is multiplied on human diploid cells such as, for example, on MRC-5 cells. The viral suspension is harvested, purified and processed by methods known in the art to give a vaccine ready for use. For this purpose, the resulting viral suspension can be clarified, e.g., by centrifugation or filtration, the viral content is then determined by methods, known in the art, e.g., using VERO cells, and the material can be stabilized by adding a sugar such as glucose, lactose and/or sucrose, and then freeze-dried.

It is possible to vary the number of passages of the virus on diploid human tissue and on fertilized poultry eggs. Suitable for the first attenuation of the mumps viruses in diploid human cells are between about 1 and 130 passages, preferably between about 1 and 5 passages, and more preferably between about 1 and 4 passages. For the attenuation in embryonic poultry eggs or fertilized poultry eggs preferred are between about 1 and 45 passages, more preferably between about 5 and 15 passages, are still more preferably between about 6 and 13 passages. Suitable for the further attenuation of embryonic poultry egg-attenuated viruses in diploid human cells are between about 1 and 149 passages, preferably between about 4 and 25 passages and still more preferably between about 11 and 19 passages. It is likewise possible to vary the temperature during incubation and cultivation, say between 30° and 38° C.

Two main purposes are attained during weakening (attenuation) and cultivation of the viruses:

(a) attenuation of the pathogenic virulence of the virus while retaining its antigenic properties, that is to say the ability to induce the formation of antibodies.

(b) Production of an attenuated virus culture which contains substantially no foreign protein—in the present case no avian proteins—and substantially no traces of antibiotics.

Having generally described the invention, a more complete understanding can be obtained by reference to certain specific examples, which are provided herein for purposes of illustration only and are not intended to be limiting unless otherwise specified.

EXAMPLES

EXAMPLE 1

Preparation Of HDC Mumps Vaccine.

(a) Preparation of the seed virus

Mumps virus were obtained from the urine of a mumps patient at the end of viremia, and purified and concentrated by differential centrifugation and ultracentrifugation for 4 hours at 25,000×r.p.m. The fraction containing mumps virus was assayed by the hemagglutination known per se test and taken up in a protein-containing medium such as Eagle's basal medium (EBM) (Gibco)+0.4% human serum albumin (HSA) and aliquots were separated thereof. Other media may also be used.

One aliquot was further processed as follows. A freshly confluent human diploid cell lawn, e.g., from Wi-38, was inoculated with the mumps suspension and, after addition of nutrient medium, e.g., EBM+10% fetal calf serum (FCS), was incubated at 37° C., the cell lawn was harvested after several days. The resulting harvest was passaged a further one to four times on human diploid cells.

Subsequently, three passages were carried out on SPF chicken eggs, with the following different inoculation and harvesting procedures being employed in each case.

(a) Inoculation into and harvesting from the allantoic cavity, (b) inoculation into and harvesting from the amniotic cavity, and (c) inoculation into the amniotic cavity and harvesting from the allantoic cavity or amniotic cavity.

The eggs were incubated at between 32° C. and 35° C. The viruses obtained after these three egg passages with the different inoculation/harvest variants described above were then pooled.

Ten further egg passages were carried out with this pool of virus by inoculation into the amniotic cavity and harvesting from the allantoic fluid. The temperature was maintained at about 32° C. The mumps antigen titer was in each case determined by the hemagglutination test.

This was followed by four rapid passages on human diploid cells (MRC-5) at about 30° C. (about 7 days for each passage). Nine further passages on MRC-5 cells at 35° C. (10–20 days for each passage) provided an attenuated seed virus.

(b) Testing of the seed virus

The seed virus obtained by the above described attenuation procedure had its identity as mumps virus tested by means of a neutralization test on VERO cells which is known in the art per se. Also tested was the virus concentration. The viral titer in VERO cells was found to be 5.6 $\log_{10}ID_{50}$/ml and the seed virus was identified as mumps virus. The viral titer indicated that production of a live mumps virus, e.g., the "Rubini" mumps virus, is possible in MRC-5 cells.

In addition, the seed virus was found to be microbiologically pure as evidenced by the following tests.

I—A bacterial test on liquid thioglycolate medium at 30°-32° C. indicated the mumps seed virus to be free of bacteria.

II—A Fungi test in liquid soya medium at 20°-25° C. evidenced the mumps seed virus to be free of fungi.

III—A Mycoplasma test in liquid and solid media found the samples to be free of mycoplasma.

IV—An in vivo Mycobacteria test in guinea pigs resulted the mumps seed virus being free of Mycobacteria tuberculosis.

V—An in vitro Mycobacteria test in liquid (Santon) media and in solid (Löwenstein-Jensen) media indicated an absence of Mycobacteria tuberculosis.

VI—A Retrovirus test for avian leucosis showed the samples to be free of retroviruses VII—An in vitro Foreign virus test in primary monkey kidney HDC (MRC-5) and lung-18 cells evidenced the mumps seed virus to be free of foreign viruses.

(c) Preparation of an HDC mumps vaccine

The seed virus was multiplied on human diploid cells such as MRC-5 cells (in compliance with WHO requirements) in culture bottles suitable for large-scale production (for example roller bottles) After one incubation step at 35° C. for 7-10 days and a microscopic assessment to detect cytopathogenic effects, the viral suspensions were harvested at intervals of one day for about 7 days. The resulting virus bulk material was stored at −190° C. under a gas phase of liquid nitrogen until the test results were obtained The virus bulk material found to be in order was thawed and clarified by filtration using a filter of pore size about 5 μm.

After diluting with a stabilizer composed of a solution of lactose, or lactose and glucose, containing human serum albumin, the "final bulk" virus thus obtained was dispensed in 0.5 ml aliquots into 3 ml vials and freeze-dried in vacuo in the frozen state.

(d) Clinical Trials

The investigations which have been carried out on human subjects up to the present date indicate that inoculation with the vaccine described above is well tolerated. Neither fever nor any local reactions have been observed. Critical organs such as, e.g., the parotid glands or testes showed absolutely no swelling, inflammation or any painful reactions. Except for one single case, all the subjects inoculated showed positive seroconversion. A single case which at a follow-up check evidenced no mumps-specific antibodies had previously also reacted negatively to other commercially available mumps vaccines.

In another clinical investigation, the resulting HDC mumps vaccine was tested in the form of a combined mumps-measles-rubella live virus human diploid cell vaccine (HDC) in a field trial against mumps, measles and rubella carried out by the double-blind method. A total of 120 infants aged from 15 to 20 months were entered in the trial. 60 children received the new vaccine and a control group of 60 children were inoculated with a known mumps-measles-rubella vaccine M-M-R$^{(R)}$ II (Merck, Sharp and Dohme). 6 to 8 week after inoculation the seroconversion rates in both groups were without exception high (95-100%). A multiple X2 test showed no statistically significant difference in the immunogenic efficacy of the two vaccines ($p > 0.05$). No reports of any side effects with the HDCV were received from any of the 12 medical groups participating in the clinical trial.

However, it was noticed that all the components of the HDC vaccine exhibit a high degree of attenuation and that the vaccine contains substantially neither avian proteins, animal protein extracts nor antibiotics. Hence all theoretical and practical contraindications because of corresponding hypersensitivities did not apply. No side effects were observed in any case.

EXAMPLE 2

Preparation Of HDC Mumps Vaccine.

(a) Mumps viruses were isolated as described in Example 1.

(b) The viruses were multiplied in diploid human cell tissue.

(c) The viruses were attenuated by 10 passages in diploid human cell tissue at 30°-35° C., 6 passages at 35°-38° C. alternately in the amniotic and allantoic sac of chicken eggs which had undergone initial incubation, and finally 6 rapid and 10 normal passages in diploid human cell tissue MRC-5 at 30°-35° C.

(d) The seed virus obtained according to (c) was multiplied (reproduced) in human diploid cells.

(e) The viruses were harvested, purified, tested, stabilized and freeze-dried as described in Example 1.

The present disclosure relates to the subject matter disclosed in Swiss Patent Application No. 05062/85-0 filed Nov. 26th, 1985 and Swiss Patent Application No. 00 86-0 filed Jan. 15th, 1986, the entire specification of which is incorporated herein by reference.

Having now fully described the invention, it will be apparent to one of ordinary skill in the art that many changes and modifications can be made thereto without departing from the spirit of scope of the invention as set forth herein.

What is claimed:

1. A method of preparing a live-attenuated mumps virus comprising the steps of:
    (i) isolating wild-type virus from a mumps-infected individual;
    (ii) adapting the isolated virus to grow on human diploid cells;
    (iii) concentrating and purifying said adapted virus;
    (iv) passaging said adapted virus on embryonated poultry eggs under conditions sufficient for enrichment of the virus;
    (v) attenuating the virus resulting from step (iv) on embryonated poultry eggs;
    (vi) further attenuating the virus resulting from step (v) on human diploid cells at 30° C.; and
    (vii) further attenuating the virus resulting from step (vi) on human diploid cells at a temperature higher than that used in step (vi) but under conditions to maintain the viability of said human diploid cells.

2. The method according to claim 1 wherein the embryonated poultry eggs are hens' eggs.

3. The mumps virus strain according to claim 1 wherein said strain is Rubini, Pasteur Institute file No. I 503.

4. A mumps vaccine comprising said live-attenuated mumps virus according to claim 3 together with a pharmaceutically acceptable carrier, wherein said live-attenuated mumps virus is present in an amount sufficient to elicit an immunogenic response in a human.

5. A method of inducing immunity to mumps in a human comprising administering to said human an immunizing amount of said mumps virus strain according to claim 3.

6. A method of preparing a live-attenuated mumps virus comprising the steps of:
   (i) isolating wild-type virus from a mumps-infected individual;
   (ii) adapting the isolated virus to grow on human diploid cells;
   (iii) concentrating and purifying said adapted virus;
   (iv) passaging said adapted virus on embryonated poultry eggs under conditions sufficient for enrichment of the virus;
   (v) attenuating the virus resulting from step (iv) on embryonated poultry eggs;
   (vi) further attenuating the virus resulting from step (v) on human diploid cells at 30° C.; and
   (vii) further attenuating the virus resulting from step (vi) on human diploid cells at 35°–38° C.

* * * * *